United States Patent [19]
Klingbeil

[11] Patent Number: 5,202,711
[45] Date of Patent: Apr. 13, 1993

[54] APPARATUS FOR EXAMINING THE FIELD OF VISION

[75] Inventor: Ulrich Klingbeil, München, Fed. Rep. of Germany

[73] Assignee: Vorrichtung zur Fesichtsfeldprufung, Ottobrunn-Riemerling, Fed. Rep. of Germany

[21] Appl. No.: 865,749

[22] Filed: Apr. 10, 1992

Related U.S. Application Data

[63] Continuation of Ser. No. 759,857, Sep. 16, 1991, filed as PCT/DE89/00643, Oct. 9, 1989, abandoned, which is a continuation of Ser. No. 477,877, Jun. 8, 1990, abandoned.

Foreign Application Priority Data

Oct. 8, 1988 [DE] Fed. Rep. of Germany ....... 3834327
Jul. 7, 1989 [DE] Fed. Rep. of Germany ....... 3922471

[51] Int. Cl.$^5$ .............................................. A61B 3/02
[52] U.S. Cl. .................................. 351/224; 351/237; 351/243
[58] Field of Search .............. 351/211, 220, 221, 224, 351/237, 243

[56] References Cited

U.S. PATENT DOCUMENTS

| | | | |
|---|---|---|---|
| 4,764,005 | 8/1988 | Webb et al. | 351/221 |
| 4,765,730 | 8/1988 | Webb | 351/221 |
| 4,768,873 | 9/1988 | Webb | 351/221 |
| 4,854,691 | 8/1989 | Sekine et al. | 351/221 |
| 4,854,692 | 8/1989 | Kobayashi | 351/221 |
| 4,893,920 | 1/1990 | Webb | 351/221 |

Primary Examiner—Rodney B. Bovernick
Assistant Examiner—J. P. Ryan
Attorney, Agent, or Firm—Antonelli, Terry, Stout & Kraus

[57] ABSTRACT

Disclosed is an apparatus for examining the field of vision, having a scanning device, which is provided with beam deflecting and beam imaging elements, via which the illumination light beam from an illumination light source is guided onto the region of the fundus oculi to be imaged and, if need be, the light reflected from the fundus oculi is guided to a detector device, from the time-sequential output signal of which an evaluation and synchronization unit generates an image of the scanned section by points, and having a control unit, which controls the intensity of the illumination light beam scanning the fundus oculi in such a manner that marks, respectively patterns, are projected onto a predeterminable region of the fundus oculi with predeterminable brightness, which the person under examination perceives, respectively does not perceive in the event of defects in the field of vision. The present invention is distinguished by the fact that in order to set a specific value of brightness of the marks, respectively of the patterns, the control unit switches the illumination light beam within the time span, during which the illumination light beam illuminates a scanning point, from a first intensity value to at least a second intensity value for a specific fraction of this time span.

20 Claims, 2 Drawing Sheets

APPARATUS FOR EXAMINING THE FIELD OF VISION

This application is a continuation of application Ser. No. 759,857, filed Sep. 16, 1991, filed as PCT/DE89/00643, Oct. 9, 1989, now abandoned, which is a continuation of application Ser. No. 477,877, filed Jun. 8, 1990 also now abandoned.

DESCRIPTION

1. Technical Field

The present invention relates to an apparatus for examining the field of vision.

2. State of the Art

The devices presently commercially available for field of view examinations have a hemispherical dish in which spots of light of adjustable brightness, also referred to as stimuli, which are distributed over the field of vision light up alternately. These spots of light of adjustable brightness are generated by light diodes attached to the hemispherical dish or by a projection system. By pressing a button, by way of illustration, the person under examination focussing on a so-called fixation mark, signals "seen" or "not seen". A control registers the response given allocating location and brightness of the lit spot of light. The result, which is usually represented in a graph, presents a "map" of the absolute o relative field view defects.

These state of the art instruments, however, have a number of disadvantages:

Although the brightness of a spot of light can be adjusted, the value of the adjusted brightness is in no strict correlation to the intensity of light actually reaching the fundus oculi as this not only depends on the brightness value of the lit spot of light, but also on the size of the pupil, etc.

Furthermore, in the state of the art devices, it must be insured that the patient focusses on the fixation mark and "does not let his eye wander around the hemispherical dish" otherwise his response "seen" gives no valid information about the lack of view field defects.

In particular, with the state of the art apparatuses it is not possible to directly correlate between the point of the lit spot of light and perhaps the pronounced, respectively pathological, structures as the person examining is unable to observe the fundus oculi directly during the field of vision examination.

Above all, the afore mentioned known instruments for examining the field of view are dependent on the "assistance" of the person under examination. i.e. they do not permit a so-called objective visus examination. In the so-called objective visus determination, the visus, that is the faculty of sight of a test person, is to be ascertained without requiring the cooperation of the person under examination. Typical applications of an objective visus determination would be the exposure of malingers for expert opinions for the courts or the visus examination of infants and pre-school children.

In scientific literature, it has been proposed to induce so-called opto-kinetic nystagmus in order to determine the visus objectively. By this is meant that the person under examination is presented a lively pattern, respectively a mark as a stimulus. If the pattern is perceived, i.e. if the structures in the pattern are large enough to be resolved by the eye, the stimulated movement causes consequent characteristic, involuntary eye movements, so-called opto-kinetic nystagmus.

Hitherto, however, there is no state of the art device with which it would be possible to determine the visus obtectively in practice.

The reason for this is that especially malingerers repeatedly succeed in intentionally looking passed the stimulus and thereby in deceiving the examining person.

Furthermore, an instrument for examining the view field has been suggested, in which a so-called scanning laser ophthalmoscope is utilized in which the intensity of the scanning light for generating the marks, respectively the stimuli, is modulated. Such devices are, by way of illustration, described in the article "Scanning Laser Ophthalmoscopy", Ophthalmology, vol. 89, No. 7 July 1982, pp. 852-857 or in the article "Reading with a Mascular Scotoma", in Investigative Ophthalmology and Visual Science, July 1986, vol. 27, pp. 1137-1147, to which, moreover, express reference is made with regard to the explanation of all details not made more apparent herein.

The use of a so-called scanning laser ophthalmoscope for examining the field of vision has the advantage that the view field examination can occur under the visual observation of the examining person as the amount of light required for generating the image of the fundus oculi is so minimal that it virtually is not disturbing as "background brightness". Furthermore, the scanning laser ophthalmosopes have, especially if they employ "pupil separation" between the entry pupil for the illumination beam of light and the exit pupil for the light reflected from the fundus oculi described in the U.S. Pat. No. 4,213,678, the advantage that the illumination beam of light passes through a small, central section of the pupil of the eye in such a manner that the illuminant reaching the fundus oculi does not depend on the size of the pupil.

Moreover, the stimuli may not only be spots of light, but also complicated patterns, such as by way of illustration Landolt rings.

In the case of the known apparatuses from the afore-cited publications, an acousto-optical modulator is used to control the intensity of the illumination light beam, which—depending whether only an image from the fundus oculi or a "stimulus" pattern is to be generated—permits a more or less large portion of the illumination light beam to pass through.

The intensity of the illumination beam of light can be varied approximately by the factor 100 with known acousto-optical modulators. Such a variation of intensity is, however, insufficient for an apparatus for field of vision examination as it is necessary to vary the light intensity physiologically by about 40 to 50 dB, by way of illustration, in order to discover the so-called relative field of vision defects, i.e. points in the view field at which bright spots of light, but not dark spots of light are still perceived.

Moreover, it is practically not possible to project a pattern with varying brightness.

This state of the art instrument also does not permit objective visus examination, but is dependent on the cooperation of the person under examination.

DESCRIPTION OF THE INVENTION

The object of the present intention is to improve an apparatus for examining the field of vision in such a manner that the intensity of the illumination beam of light can be varied at least by 40 dB or more. Another object of the present invention is to provide a device for an objective examination of the field of vision, respectively for an objective visus determination, with which, in particular, the visus of people who want to deceive the examining person about their faculty of sight can be objectively ascertained.

A solution to the first object in accordance with the present solution is characterized in setting a specific brightness value for the marks (pattern), respectively stimuli, the control unit switches the illumination beam of light at least once from a first intensity value to a second intensity value within a time span, during which the illumination beam of light scans a scanning point. This second intensity value may, in particular, have the value zero, i.e. the control unit switches the illumination beam of light off at least once for a specific fraction of this time span.

According to the present invention, thus the intensity of the illumination beam of light is not constant during the illumination of a "scanning point" as is the case in the state of the art devices. As on the other hand, the duration of the illumination of a scanning point—depending on the number of "pixel" taken—is approx. 100 ns, this switching of the illumination light beam, which inevitably results in "pulse durations" of less than 100 ns for the individual intensity values, is not noticed by the person under examination. But rather the retina of the person under examination registers a mean value of brightness corresponding to the temporal integral over the incident light intensity.

By means of this invented measure, the brightness of the marks inscribed by the illumination beam of light can be varied within a substantially greater framework than is the case with the state of the art apparatuses, in which the transmission factor of the acousto-optical modulator is varied between a minimum and a maximum value with the transmission factor of the acouto-optical modulator not changing during the "scanning of a point". In particular, marks can also be generated in this way "containing a series of scanning points" and in which brightness is varied in such a manner that the variation is resolved by the human eye. This can, by way of illustration, be advantageous in examining so-called receptive fields.

Furthermore, in accordance with the present invention, the visus of a person under examination can he determined while simultaneously controlling fixation.

An element of the present invention is that, by switching the light beam from the illumination light source of such scanning ophthalmoscopes between at least two degrees of brightness, patterns are projected onto the fundus oculi thereby triggering an opto-kinetic nystagmus and that at the same time the involuntary eye movements caused by projecting the patterns are tracked.

In this case, it is especially advantageous if the "normal" brightness of the scanning light beam in a scanning opthalmoscope may be so small that it can remain below the "stimulus threshold". That is to say that the person under examination does not perceive the projected patterns on a "very high level of brightness" as would, by way of illustration, be required if the fundus oculi were examined with a conventional fundus camera with an areal illumination light source during the projection of the pattern.

Furthermore, it is advantageous if, random patterns can be easily generated by the modulated illumination light beam, whereby the patterns can be moved without difficulty over predetermined regions of the fundus oculi.

The reaction of the person under examination can, by way of illustration, be visually controlled by the examining person on a monitor, on which an image of the fundus oculi is represented. However, it is particularly advantageous if with the invented development, with which the projection of the patterns is simultaneous with the representation of the fundus oculi, the control and evaluation unit registers the movements of the eye and correlates them to the point on the fundus oculi, onto which the pattern or patterns were projected. In addition, according to claim 6 hereto, the voluntary eye movements can be compensated via so-called "fundus tracking" as is known in principle in the field of ophthalmology.

As the invented apparatus automatically recognizes if the shown structure is seen by the person under examination, moreover, by varying the brightness of the light beam more than two degrees or by continually varying it, automatic visus threshold value measuring can also be carried out, in which the structure when recognized is successively reduced in brightness, respectively the size of the structure is successively decreased, until the so-called opto-kinetic nystagmus is no longer triggered. Naturally, the invented apparatus can also be operated in the conventional manner so that the person under examination responds "seen" or "not seen", by way of illustration, by pushing a button. The control unit, which by way of illustration, may be provided with a conventional micro-computer, stores the response of the person under examination in correlation to the position, the size and the brightness of the respective pattern, respectively mark.

In order to keep irritation of the person under examination by the "normal illumination light" to a minimum, it is in addition also possible with the invented apparatus to work with two wavelengths, thus, by way of illustration, to conduct the normal fundus examination with infrared light, which the person under examination does not perceive, and only to fade in visible light in order to project the pattern, respectively the marks.

Naturally, the control unit can also vary the intensity of the illumination light beam. This can, by way of illustration, occur in the event a light diode or a laser diode is utilized as the illumination light source, by varying the operational voltage of the diode.

The switching, respectively switching off and subsequently switching on, may, of course, occur in the most varied ways, by way of illustration, by switching the illumination light source on and off accordingly.

Furthermore, the control unit can be provided with an acousto-optic modulator arranged in the path of the illumination beam. This acousto-optical modulator may in this case serve to adjust the intensity value of the illumination light source or it can be triggered with high-frequency in such a manner that, while the images are being generated, it blocks the light path "most of the time" at those points at which only the fundus oculi is to be imaged and thereby only lets a small part of the illumination light beam pass, whereas with a scanning device, in which the marks are to be inscribed, it opens the path of the illumination light a bigger fraction of the scanning time and thereby permits a larger part of the illumination light to pass.

Moreover, an additional light source is provided, which generates the background brightness so that the field of vision examination takes place "on a specific level of ambient brightness". It is expressly pointed out that the desired "ambient brightness" can also be adjusted by the scanning illumination light beam, which also can generate "on the average" a certain "background brightness".

Apparatuses for examining the view field have, compared to other field of vision examination devices, in which light diodes are provided for generating the marks, the advantage that "stimuli" can be generated at any points in the field of vision of freely predetermined shape. For this reason, the control unit is preferably provided with a so-called (image) memory, in which the position, shape and brightness of the marks are stored, which are to be presented consecutively to the person under examination and which possibly stores the response of the person under examination allocating it to the position and size, respectively brightness, of the respective mark, respectively "involuntary" movements of the eye that might occur. It is evident that in this case certain procedures in presenting the individual marks may be followed as may be known from the patent literature or from devices of the present applicant. In particular, information can first be elicited from marks which are roughly distributed over the field of vision; the detected defects can subsequently be "picked-up" more closely.

The invented apparatus has the special advantage that the individual data of the marks can be stored allocating them to the image recorded, respectively of the pronounced points of the fundus: in order to do this, an image is made of the fundus under examination by raster projection, respectively mark projection and the position of a pronounced fundus structure is simultaneously analyzed. For this purpose, such a fundus structure (templet) is selected prior to starting the examination. With all the images subsequently made during each raster projection, how far the marked structure has shifted from the position of the structure in the original or the preceding image is examined. This can occur automatically via so-called fundus tracking or semi-automatically via marking the pronounced structure. The shifts respectively detected are utilized to compensate for the movements of the fundus during the examination, respectively to subsequently correct the raster position.

This tracking permits for the first time an examination of field of vision sensitiveness in conformance to the position.

The digital storage of the position, size and brightness of the individual marks as provided for in accordance with the present invention is advantageously further improved by the brightness of the marks is stored, by way of illustration, as an 8-bit value. As only a scale of two and a half can be represented with 8 bits, in accordance with the present invention the stored 8-bit value is allocated non-linearly to a specific brightness value. This can, by way of illustration occur by first converting the 8-bit value stored in the image memory digitally/analogously and the analogously converted value is transformed by at least one logarithmic amplifier with fixed or programmable amplification into a grey value, i.e. a value of brightness.

A BRIEF DESCRIPTION OF THE DRAWING

The present invention is made more apparent by way of illustration in the following section without the intention of limiting the overall scope of the inventive concept using preferred embodiments with reference to the accompanying drawing, to which, moreover, express reference is made with regard to the disclosure of all the invented details not made more apparent herein:

A DESCRIPTION OF A PREFERRED EMBODIMENT

Figure 1:
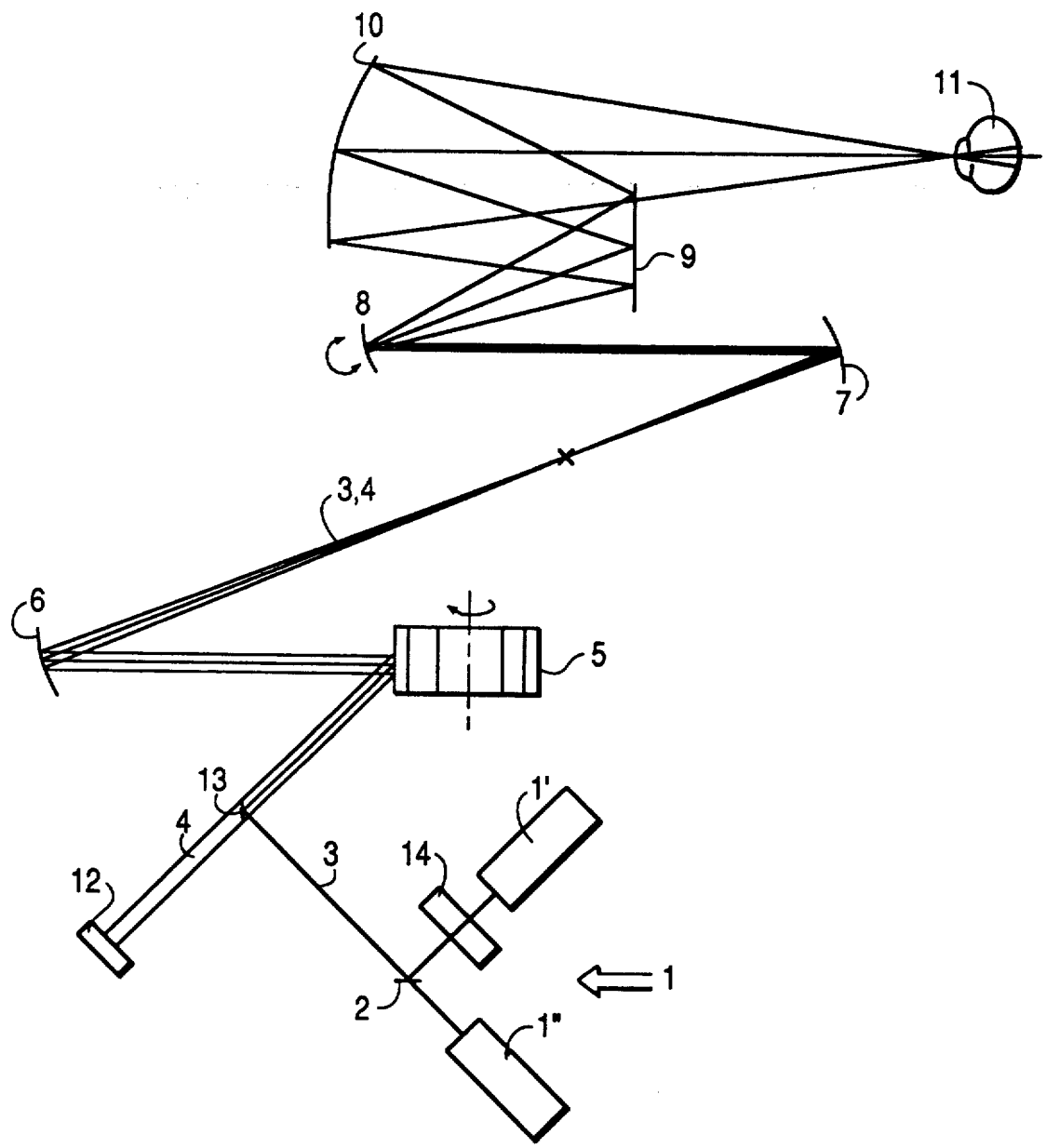
FIG. 1 shows the basic construction of an invented apparatus.

The invented apparatus can, by way of illustration, be realized with a laser scanning ophthalmoscope in the manner described in WO 88/033 96. This apparatus has an illumination light source 1, which in the case of the depicted preferred embodiment is composed of two lasers 1' and 1" operating with different wavelengths and by means of a mirror 2 alternately or jointly generate an illumination light beam 3. In the case of the depicted preferred embodiment, both the illumination light beam 3 and the light beam 4 coming from the fundus oculi "pass" via the deflection device, which is made more apparent in the following.

The light beam 3 from the illumination light source 1 is deflected in a horizontal direction by a horizontal scanner, which in the case of the depicted preferred embodiment is a rotating polygonal mirror 5. The beam thus fanned out in the horizontal plane passes mirror system 6 and 7 and strikes a vertical scanner, which in the case of the preferred embodiment is an oscillating mirror, respectively a galvanometer mirror 8. Behind mirror 8, the bundle of beams has a "rectangular" cross-section. Following the deflection on a plane mirror 9, it is imaged upon the eye under examination 11 by a concave mirror 10. The beam of light 4 reflected at the fundus oculi passes the afore-mentioned elements in reverse order and is indicated behind the horizontal deflection element 5 by a detector unit 12 following prior separation of the paths of the illumination and examination light by means of a mirror 13. Combining the mirrors as imaging elements yields a number of advantages, such as minimal imaging errors, no reflexes, achromaticity and minimal space requirements due to folding the beam path. Whereby achromaticity is especially important if the illumination occurs simultaneously with laser light of differing wavelengths, by way of illustration in the infrared range and the visible range.

Divider mirror 13 separating illumination light path 3 and examination light path 4 is, in the case of the preferred embodiment, a small mirror so that the exit pupil of the reflected beam path 4 encircles the entry pupil. Naturally other divider mirrors 13 may also be utilized, which, by way of illustration, result in the entry pupil and the exit pupil being superimposed.

Furthermore, an acousto-optical modulator 14, which lets the light, by way of illustration, emitted from laser 1' pass in one switched state and blocks it in the other switched state, may be provided in illumination light path 3. In this event, the switching on and off of the modulator happens so fast the light path is blocked at least once during each illumination period. The acousto-optical modulator 14 may also be employed to adjust the intensity of the laser beam "integrally", whereby switching between the two values of intensity then occurs, by way of illustration, by appropriate triggering of the laser. This imaging is preferred with the "speed" of the present commercial modulators. The illumination period of an image point, of course, depends on the number of images generated and on the number of image points per image, with the usual video norm it typically amounts to 100 ns.

As the time during which the light path is blocked necessarily has to be less than 100 ns, the eye does not perceive the switching on and off procedure, but rather "only sees an average integrated intensity".

Figure 2:
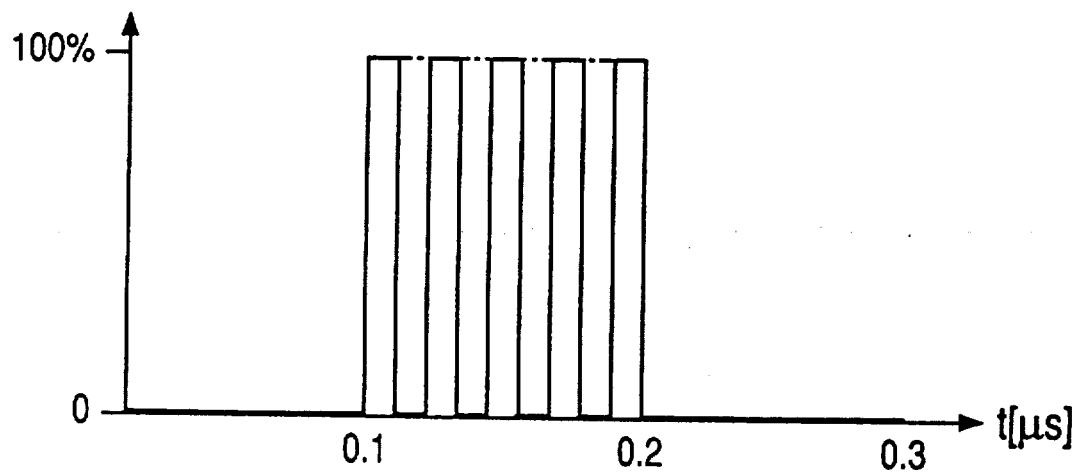
FIG. 2 shows the principle of the invented variation of brightness.

FIG. 2 depicts this schematically for the event that the illumination light beam is switched off and respectively on again four times during the period of illumination of an image point so that a total of five illumination periods are yielded. The actual intensity perceived by the eye depends on the ratio switch-on time/switch-off time.

Figure 3:
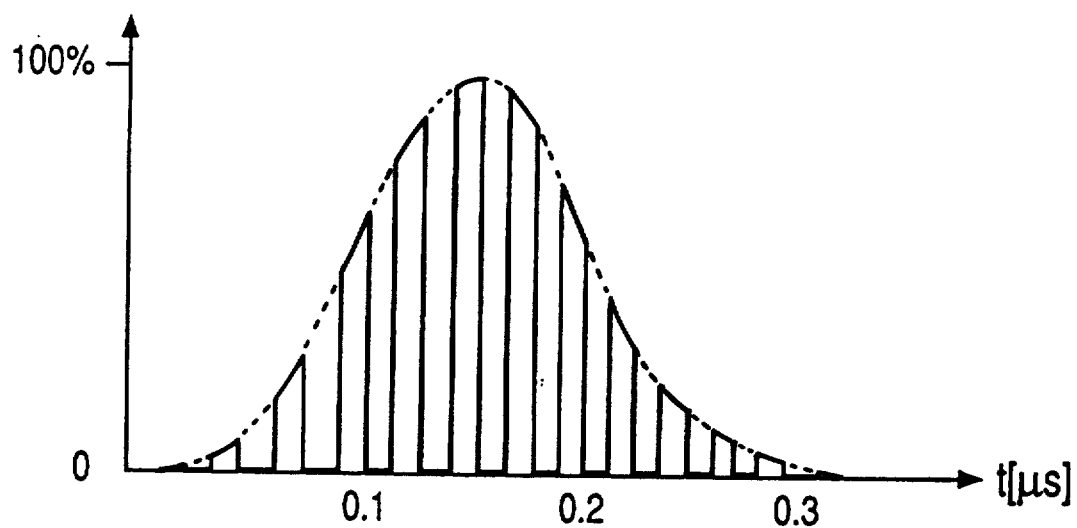
FIG. 3 shows the invented variation of brightness in conjunction with the additional variation of intensity.

FIG. 3 depicts schematically the event that the intensity of the laser beam is additionally varied, by way of illustration by, acousto-optical modulator 14 or appropriate triggering by lasers 1', respectively 1".

The combination of switching the light beam on and off in connection with varying the intensity permits varying the brightness perceived by the eye by at least 50 dB.

In the preceding section the present invention has been described using a preferred embodiment without the intention of limiting the scope of the overall inventive concept. Thus, other devices than the one described herein can be utilized as "basic apparatuses". Furthermore, it is expressly pointed out that any sources of light, i.e. even light sources other than lasers, may be employed as light sources.

Moreover, an additional illumination light source can be provided, which generates a "background brightness" or permits making an infrared image. As the eye does not perceive the infrared light, it is, therefore, possible to check whether very dark light spots can be perceived at low background brightness. Nonetheless, the invented apparatus permits visual examination of the position of the pattern projected onto the fundus oculi.

In addition to this, the invented apparatus can be utilized for measuring evociated potentials or other electrophysical data. Other measures can also be used instead of the acousto-optical modulator for switching the illumination light beam on or off. By way of illustration, the light source can be switched on or off.

The control unit not described in the preceding, which controls the light spots and, if need be, tracks in the event of eye movements, can be realized in an as such known manner, by way of illustration with a microcomputer.

What is claimed is:

1. An apparatus for examining the field of vision, having a scanning device, which is provided with beam deflecting and beam imaging elements, via which an illumination light beam from an illumination light source is at least one of guided onto the region of the fundus oculi to be imaged and the light reflected from the fundus oculi is guided to a detector device, from the time-sequential output signal of which an evaluation and synchronization unit generates an image of the scanned section by points, and having a control unit, which controls the intensity of the illumination light beam scanning the fundus oculi in such a manner that marks are projected onto a predetermined region of the fundus oculi with predetermining brightness, which the person under examination perceives or does not perceive in the event of defects in the field of vision, wherein, in order to set a specific value of brightness of said marks, said control unit switches said illumination light beam within a time span, during which said illumination light beam illuminates a scanning point, from a first intensity value to at least a second intensity value for a specific fraction of said time span which is sufficient for a field of vision examination.

2. An apparatus according to claim 1, wherein said control and evaluation unit detects movements of the eye for objective visus examination and correlates them with the position on said fundus oculi, on which at least one of said marks is projected.

3. An apparatus according to claim 1 or 2, wherein said control unit stores the response "seen" or "not seen" from the person under examination allocating them to the position, size and brightness of said respective pattern, respectively of said mark.

4. An apparatus according to claim 1, wherein said control and evaluation unit adjustably alters the brightness and/or size of said patterns and/or their velocity.

5. An apparatus according to claim 4, wherein said control and evaluation unit adjusts the brightness value of said light beam for generating the marks in more then two steps or continuously.

6. An apparatus according to claim 1, wherein said control and evaluation unit compensates for eye movements.

7. An apparatus according to claim 1, wherein said control unit switches said illumination light beam off at least once within said time span, during which said illumination beam illuminates a scanning point, i.e. said second intensity value is zero.

8. An apparatus according to claim 1, wherein said control unit in addition varies said intensity of said illumination light beam in order to switch said intensity value between two intensity values.

9. An apparatus according to claim 1, wherein said control unit is provided with an acousto-optical modulator, which is arranged in the path of said illumination light beam.

10. An apparatus according to claim 1, wherein said control unit switches said illumination light source, respectively turns it on or off.

11. An apparatus according to claim 1, wherein an additional light source is provided, which generates a background brightness.

12. An apparatus according to claim 1, wherein said illumination light source emits light of a different wavelength to examine the fundus oculi than to project the patterns.

13. An apparatus according to claim 1, wherein said control unit is provided with a memory, in which the position, shape and brightness of said marks are stored.

14. An apparatus according to claim 13, wherein the data of said marks are stored allocating them to the image taken, respectively to pronounced fundus points.

15. An apparatus according to claim 14, wherein said control unit corrects in the event of eye movements the position of the lit mark and/or the allocation of the just lit mark to said fundus oculi.

16. An apparatus according to claim 15, wherein said brightness of said marks is stored as a digital value and the allocation of a brightness to a digital value is not linear.

17. An apparatus according to claim 16, wherein said control unit is provided with a digital/analogous converter, which converts said digital value to an analogous value and after which at least one non-linear amplifier is connected, the output signal of which indicates the value of said brightness.

18. An apparatus according to claim 1, wherein said control unit controls the intensity of the illumination light beam so as to vary the light intensity by at least 40 dB.

19. An apparatus according to claim 1, wherein said control unit switches said light beam on and off with the illumination light beam being switched off for less than 100 ns.

20. An apparatus according to claim 1, wherein the marks are projected as a pattern.

* * * * *

UNITED STATES PATENT AND TRADEMARK OFFICE
CERTIFICATE OF CORRECTION

PATENT NO.   :   5,202,711
DATED        :   Apr. 13, 1993
INVENTOR(S)  :   KLINGBEIL, et al

It is certified that error appears in the above-identified patent and that said Letters Patent is hereby corrected as shown below:

<u>ON THE TITLE PAGE</u>

[75]   Inventor:   Ulrich Klingbeil, Munchen, Fed. Rep. of Germany and Andreas Plesch, Munchen, Fed. Rep. of Germany

[73]   Assignee:   G. Rodenstock Instrumente GmbH, Ottobrunn-Riemerling, Fed. Rep. of Germany Signed and Sealed this Twentieth Day of December, 1994

Attest:

BRUCE LEHMAN

*Attesting Officer*     *Commissioner of Patents and Trademarks*